United States Patent
Yang

(10) Patent No.: US 8,798,719 B2
(45) Date of Patent: Aug. 5, 2014

(54) METHOD OF UTILIZATION OF HIGH DIELECTRIC CONSTANT (HDC) MATERIALS FOR REDUCING SAR AND ENHANCING SNR IN MRI

(76) Inventor: Qing X. Yang, Hummelstown, PA (US)

( * ) Notice: Subject to any disclaimer, the term of this patent is extended or adjusted under 35 U.S.C. 154(b) by 672 days.

(21) Appl. No.: 12/958,385

(22) Filed: Dec. 1, 2010

(65) Prior Publication Data

US 2011/0152670 A1    Jun. 23, 2011

Related U.S. Application Data

(60) Provisional application No. 61/266,109, filed on Dec. 2, 2009.

(51) Int. Cl.
*A61B 5/00* (2006.01)

(52) U.S. Cl.
USPC ............................ 600/421; 324/307; 324/318

(58) Field of Classification Search
None
See application file for complete search history.

(56) References Cited

U.S. PATENT DOCUMENTS

| | | | |
|---|---|---|---|
| 5,928,145 A * | 7/1999 | Ocali et al. | 600/410 |
| 6,252,403 B1 * | 6/2001 | Alsop | 324/318 |
| 6,454,711 B1 * | 9/2002 | Haddad et al. | 600/371 |

* cited by examiner

*Primary Examiner* — Unsu Jung
*Assistant Examiner* — Amanda Lauritzen Moher
(74) *Attorney, Agent, or Firm* — McNees Wallace & Nurick LLC

(57) ABSTRACT

Layers or coats of materials with high dielectric constant or permittivity with very low conductivity are inserted in between radiofrequency (RF) coil or coil's conductive elements and the sample to enhance the signal to noise ratio (SNR), improve image contrast, and reduce the specific absorption rate (SAR) of magnetic resonance imaging or magnetic resonance spectroscopy instruments. The embodiments of the present invention can be used as an auxiliary device to the standard pre-constructed RF coils or incorporated with RF coil constructions for enhancing RF coil performances in both transmission and reception.

18 Claims, 5 Drawing Sheets

METHOD OF UTILIZATION OF HIGH DIELECTRIC CONSTANT (HDC) MATERIALS FOR REDUCING SAR AND ENHANCING SNR IN MRI

This application claims priority to and benefit of U.S. Provisional Patent Application No. 61/266,109, filed Dec. 2, 2009, and PCT Patent Application No. PCT/US2010/058625 filed Dec. 2, 2010, titled "A Method of Utilization of High Dielectric Constant (HDC) Materials for Reducing SAR and Enhancing SNR in MRI," which are both hereby incorporated by reference in their entirety.

STATEMENT AS TO RIGHTS TO INVENTIONS MADE UNDER FEDERALLY SPONSORED RESEARCH OR DEVELOPMENT

This research was supported by Grant No R01 AG02771 from the NIH. The Government has certain rights in the invention.

BACKGROUND OF THE INVENTION

1. Field of the Invention

This invention relates generally to the radiofrequency (RF) electromagnetic field, denoted as B1, used for magnetic resonance imaging (MRI) and magnetic resonance spectroscopy (MRS) spectroscopy instruments. Particularly, the invention relates to the use of materials with high dielectric constant (HDC) or permittivity with low electrical conductivity for RF field generation in the MRI or NMR instruments.

2. Description of the Prior Art

RF coils are used to produce RF magnetic field (B1) for excitation and detection of the magnetization signal from an object such as parts of human body during MRI and MRS data collections. The RF field can be generated by a coil or a set of coils. The RF field is transmitted into the sample or human body to excite the nuclear spins. Subsequently, the RF signals from the nuclear spins are received by the same or a different set of RF coils. The present invention improves the efficiency of RF coils for both transmission and reception of the B1 field. The efficiency of a RF coil includes B1 field uniformity and intensity in a region of interest (ROI) produced by unit input current. In general, a stronger B1 field generated by a RF coil with unit input current translates to better reception sensitivity and lower RF heating of the tissue samples that may be hazardous to human body when it reaches to a certain level. The reception sensitivity of a RF coil is experimentally determined by measured image signal to noise ratio (SNR) from an ROI obtained with standardized imaging protocols, and the heating effect by RF field can be assessed numerically with calculation of Specific Absorption Rate (SAR) distribution in the human body (1).

The SNR of an MR image is critically important for the quality of the image as MRI is an intrinsically low SNR instrument. Significant amount of efforts and resources have been invested in order to gain higher image SNR in a given image data acquisition time. In particularly, this includes the use of higher static magnetic field strength from current 1 to 1.5 Tesla to 3 to 7 Tesla, which is extremely expensive. Unfortunately, an increase in static magnetic field strength leads to a higher frequency of RF field, which, in turn, dramatically increases RF heating effect of the tissue (1) and creates RF field inhomogeneity artifacts (2-5). These two problems pose serious challenges for high field MRI development in human imaging. The present invention introduces a novel method of use of HDC materials that increases B1 field intensity inside the sample and reduces SAR in the sample during image acquisition.

The recent experimental data in high field (3-8 Tesla) human imaging systems demonstrated that high dielectric constant of human body plays an important role for RF field behavior in human body in high field. The electrical properties, geometry, and relative position of the sample in the coil become important factors in determining the B1 field distribution inside the sample (6-11). Consequently, adjustment of B1 field distribution inside the sample or human body and the coupling between the sample and coil can be facilitated with HDC materials. Foo, et al. proposed a method of correcting for the RF inhomogeneity in human body observed on a 4 Tesla MRI system by "dielectric loading of the coil-to-shield space in an RF resonator (coil and shield assembly)" (10). Based on Foo's theoretical analysis, he proposed to adjust the RF homogeneity by loading the coil-to-shield space with dielectric material of suitable relative permittivity so as to alter the propagation constant of the coil. With theoretical calculations, Foo predicted that a value of between 30 and 40 for the relative permittivity of the dielectric material in the coil-to-shield space would reduce the RF field inhomogeneity from +/−15% to about +/−3% over a central 30-cm-diameter region of a homogeneous 40-cm-diameter body at both 64 MH and 170 MHz corresponding to a 1.5 and 4 Tesla MRI system respectively. However, their experimental results at 4 Tesla showed that "the improved RF field homogeneity would be accompanied by increased RF power requirements and reduced coil sensitivity." There at least three distinctive differences in Foo's work from the present invention. 1) The dielectric material is inserted in the coil-to-sample space in the present invention, while it was loaded in "the coil-to-shield space" in Foo's work. In fact, the dielectric material is placed in the opposite side of the RF coil of the present invention. As demonstrated in their experimental results, Foo's approach produced totally opposite outcome i.e. a "increased RF power requirements and reduced coil sensitivity". 2) The theoretical bases are totally different. In the present invention, the HDC material is used to couple the RF field produced by the RF coil with the sample. In Foo's work, the dielectric material was used to manipulate "the axial propagation constant of RF resonator" itself. 3) In Foo's work, the choice of dielectric material was based on the specific design and geometry of the RF coil or resonator. In principle, the present invention requires no knowledge of the RF coil configuration. It is more effective, however, that HDC-pads of the present invention are developed to fit a specific coil design for optimal effect.

To address the same RF field inhomogeneity issue in the head image taken at 4 Tesla, Alsop et al. presented a novel spiral RF volume coil design for high field MRI use (2). Images acquired with his spiral coil design showed a signal drop on the top of the human head. It was attributed as the abrupt change in dielectric property between tissue and air at the top of head since his coil design theoretical analysis was based on a mathematical model of an infinite long cylinder. To mitigate this additional problem associated with the spiral coil design, a dielectric pad at the end of the coil was included during image data collection. In his work, the introduction of a dielectric pad was specifically used only for compensation of the signal drop caused by the use of spiral coil. In the present invention, HDC-ads are placed inside an RF volume coil of any design to improve the efficiency of a given RF coil.

SUMMARY OF THE INVENTION

It is desirable to have a strong and uniform B1 distribution in entire sample being imaged. It is an object of the present invention that materials (liquids, solids or mixtures) with high dielectric constant (HDC) or permittivity are incorporated into RF coils to change the RF field to a desirable distribution inside the sample. Here the word "high" refers to the value of dielectric constant of a material that is higher than that of the tissue of the sample under investigation at the frequency transmitted and received by the RF coil. The presently preferred embodiments are in forms of a pad or pads filled with HDC materials, referred as HDC-pad thereafter.

It is another object of this invention that HDC materials are incorporated into RF coils to reduce the transmission power for a given excitation flip-angle in a region of interest (ROI) inside the sample.

It is another object of this invention that HDC materials are incorporate into a or a set of RF receive coil to enhance the image SNR of the sample.

For certain applications in the art, it is desirable to have a strong and uniform B1 only in a part of the sample or a ROI in the sample. It is another object that HDC materials are incorporated into the coil or inside the sample to enhance an RF coil performance in term of an increase in SNR in a ROI near or around HDC materials in the sample and a decrease of input RF power, therefore, SAR in the sample during excitation of magnetization.

It is another object of this invention that HDC materials are used as a RF field trap to reduce radiation loss of high field MRI coils. In high field MRI (3 T, 4 T, 7 T and above), radiation loss becomes more significant as the corresponding RF field frequency increases.

It is anther object of this invention that HDC materials are used as contrast enhancement agents.

The principle of this invention is to insert layers or coats of materials with high dielectric constant and very low conductivity in between RF coil or coil conductive elements and sample. The HDC materials stated herein can be solids, such as ceramics, or liquids, such as water, deuterium or water-based jell or suspensions of any dielectric additives to adjust the dielectric constant. The geometry, amount, mechanical and electric properties of the HDC material best suited for the embodiments of the present invention will depend on specific applications, RF coil configuration and the resonance frequency of the RF field. For water-based jell pad, the signal from the pad can be removed by addition of a small amount of Manganese Chloride ($MnCl_2$) or any other NMR signal relaxing compound or by replacing water with deuterium ($D_2O$).

BRIEF DESCRIPTION OF THE DRAWINGS

The foregoing and other novel features and advantages of the invention will become more apparent and more readily appreciated by those skilled in the art after consideration of the following description in conjunction with the associated drawings, of which:

FIG. 5 Calculated $B_1^+$ maps at 128 MHz in three orthogonal planes with (top row) and without the HDC-pad (middle). The $B_1^+$ distributions along the dotted lines in the corresponding maps are plotted on the bottom. All the $B_1^+$ maps are scaled to 1 W input power.

DETAILED DESCRIPTION OF THE PRESENTLY PREFERRED EMBODIMENTS

Figure 1:
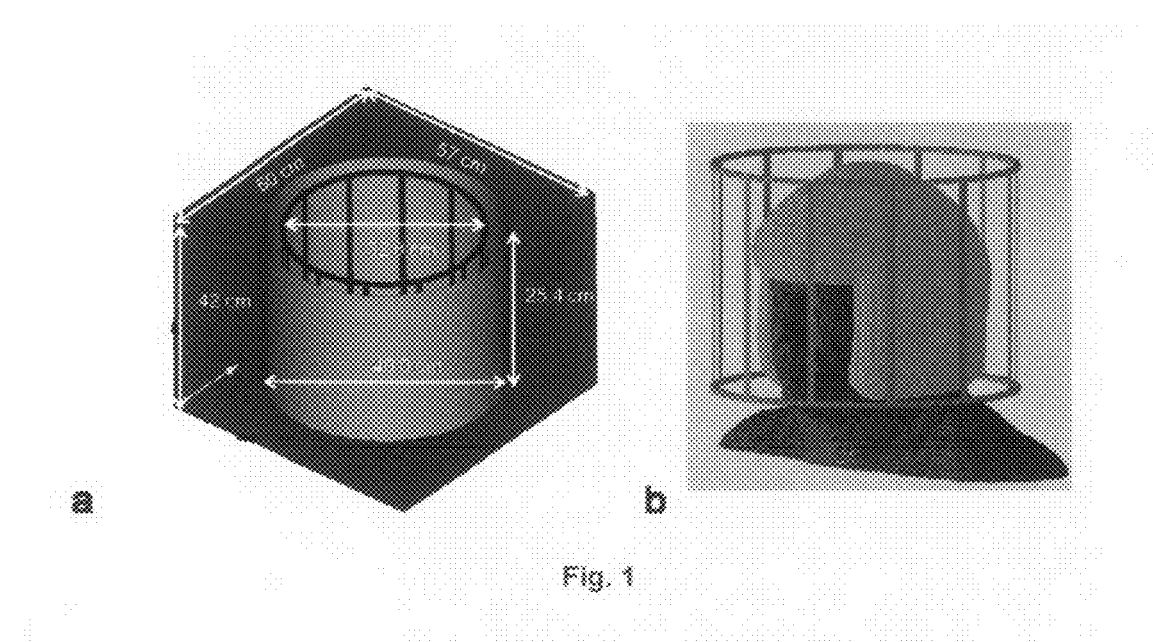
FIG. 1 Computer models of the bird-cage coil (a) and human head with the HDC-pad (b).

A preferred embodiment of the present invention will now be described in detail with reference to FIGS. 1-5. Those skilled in the art will appreciate that the description given herein with respect to those figures is for exemplary purposes only and is not intended in any way to limit the scope of the invention. All questions regarding the scope of the invention may be resolved by referring to the appended claims.

Theoretical Considerations

For conductive dielectric materials such as human brain tissues, the RF field inside the sample is perturbed by conductive current ($J_c$) and displacement current ($J_d$) according to Ampere's Law with Maxwell's correction, $$\nabla \times B = \mu J_c + \mu J_d = \mu \sigma E + i\mu \epsilon_r \epsilon_0 \overline{\omega} E \quad [1]$$

where B is magnetic flux density, E is electric field, $\overline{\omega}$ is angular frequency, $\epsilon_r$ is relative electric permittivity (dielectric constant), $\epsilon_0$ is the electric permittivity in vacuum, $\sigma$ is electrical conductivity, m is magnetic permeability, and $i = \sqrt{-1}$ is the complex unit which introduces a 90-degree phase difference between conductive current and displacement current (Johnk 1988). For plane waves travelling in a homogeneous medium, the conductive current leads to decay of the RF field in the direction of propagation, while the displacement current with a 90° phase shift acts as a secondary field source facilitating RF wave propagation. In this case, the opposing contributions of the two sources to B1 can be considered using ratio $J_c$ and $J_d$ given by $$J_c/J_d = \sigma/\overline{\omega} \epsilon_0 \epsilon_r.$$

In principle, materials with low $\sigma$ and high $\epsilon_r$ can enhance the local B1 field strength for a RF field frequency range high enough to induce the displacement current much stronger conducting current. This equation describes the relationship within the dielectric materials. Subsequently, the RF wave propagates into the sample with stronger amplitude enhanced by the HDC materials. Thus, in general, placement of HDC-pads near a ROI in MRI should result in enhanced local B1 field strength with concomitant improvement of SNR and reduction of overall SAR.

HDC-pad Design for Human Head Imaging

FIG. 1b illustrates geometry and configuration related to the RF coil and the human head of the preferred embodiment of present invention. The embodiment of present invention is a HDC-pad in a form of a helmet, containing approximately 6 liters of distilled water, was conformed around the superior portion of the head, extending to just above the level of the eyes in front, just above the ears on the sides, and just below the end of the skull in the back of the head. The thickness of the HDC-pad is 3 mm.

Computer Modeling

The quantitative evaluation on how placement of a HDC-pad changes the B1 field distribution depends on the detailed geometries and sizes of the coil and sample, the embodiment of present invention, thus, must be determined numerically with computer modeling. In the following a computer modeling on a HDC-helmet is used to demonstrate the efficacy of the invention.

A numerical model with finite difference time domain (FDTD) method was used to calculate the RF field distribution in the sample and coil model shown in FIG. 1a at 128 MHz corresponding to a static magnetic field strength of 3 Tesla. All the FDTD calculations were performed with commercially-available software (XFDTD; Remcom, Inc, State College, Pa.), and post-processing of the simulation results was performed with home-built programs in MATLAB (The Mathworks, Inc., Natick, Mass.). A 3D mesh with isometric 2 mm resolution was created within a region of 57×50×42 cm$^3$. The calculation was performed with −35 dB convergence to ensure that the steady state was reached. A Liao boundary condition was used for the outer boundary truncation of the grid (12). The coil was modeled after that used in experiment: a copper 12-rung high-pass birdcage coil (32.8 cm i.d. and 25.4 cm length, shield diameter of 40.0 cm). The coil model was driven using 24 current sources spaced evenly on the two end rings, at the locations of capacitors in the actual coil. The human head model used for the FDTD calculation included 16 types of tissue and the corresponding electric properties at 128 MHz were HDC-pad was modeled with a 3 cm thick uniform layer of water ($\sigma$=0.0047 S/m$^2$, $\in_r$=78) over the head excluding the face as shown in FIG. 1b (13).

Experimental Measurements

Human brain images were acquired on a 3 T whole body system (Bruker, Biospin, Ettlingen, Germany) using a quadrature 12-element high-pass birdcage coil with 26 cm inner diameter and 29 cm length. Axial brain images were acquired with identical imaging parameters with and without a HDC-pad placed around the head and after the coil was tuned and matched, and RF power was calibrated for each condition. The subject remained in the magnet during the process of placing and/or removing the HDC-pad, re-tuning the coil and adjustment of RF power for 90°/180° flip angle. Input power for the flip angle was adjusted manually with and without the HDC-pad while maximizing the total signal on 5 axial slices covering a 2.5 cm slab through the center of the brain. Fast spin-echo (RARE) images with slice thickness=5 mm, matrix=128×128, FA=180°, and FOV=30 cm were acquired on five axial, sagittal, and coronal planes spaced 5 mm apart through the cerebrum. The experiment was repeated four times with two human subjects. All of the subjects provided written informed consent prior to participation, in accord with the requirements of the Institutional Review Board of the Pennsylvania State University College of Medicine.

Figure 2:
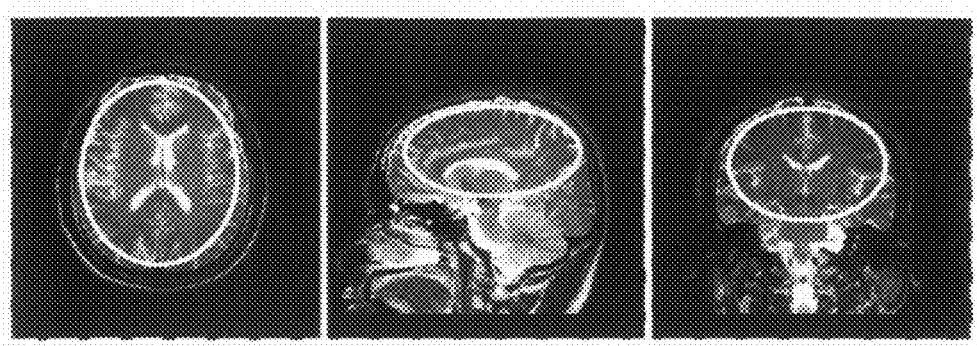
FIG. 2 Examples of elliptical ROI used to evaluate T2-weighted image intensity for SNR measurement and uniformity assessment on mid-axial (left), sagittal (center), and coronal (right) planes.

Signal-to-noise ratio (SNR) was measured using the magnitude images acquired under the above two conditions. The average signal intensity was calculated in an elliptical ROI covering most of the cerebrum in each of the 15 images acquired with and without the HDC-pad. Examples of the elliptical region in each orientation are shown in FIG. 2. The noise was measured by calculating the standard deviation in an ROI covering 29 cm$^2$ in a region of no visible signal or artifact across the top of each image.

Results

Figure 3:
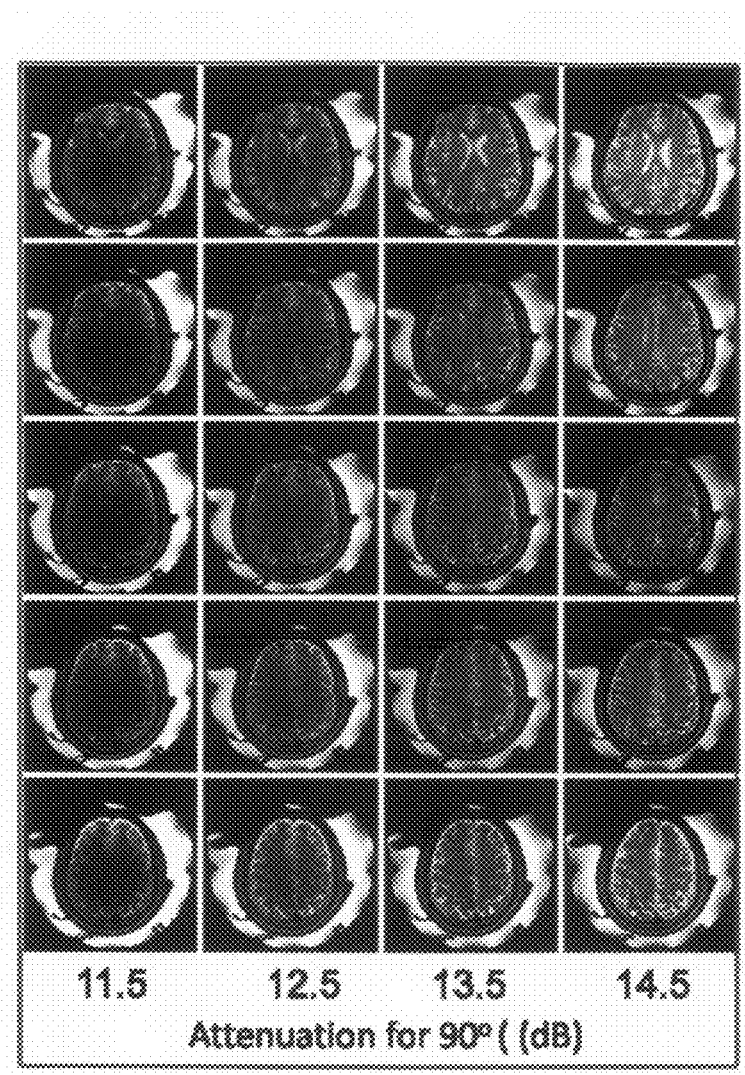
FIG. 3 Addition of HDC-pad resulted in dark regions in central regions of all brain images due to overtipping (left columns) with the RF power level optimized without the HDC-pad. The images on right columns were acquired using input RF power with attenuation values listed below. The images on the far right column were obtained with final power attenuation for 90° flip angle was 14.5 dB, 3-dB more attenuation than that of without the HDC-pad.

FIG. 3 shows a set of axial images of human brain after addition of the HDC-pad and re-tuning of the coil, but before re-optimization of the RF power levels (using power values optimized without the HDC-pad) on the left columns, and images with the HDC-pad using the RF power levels indicated at the bottom of columns of the images. After addition of the pad, the RF power levels that previously generated 90°/180° excitation/refocusing pulses in the brain created much larger flip angles due to enhancement of the $B_1$ field. A 3-dB reduction of power for both the excitation and refocusing pulses was required to maximize the signal and imagins were acquired shown on the far right column in FIG. 3.

Figure 4:
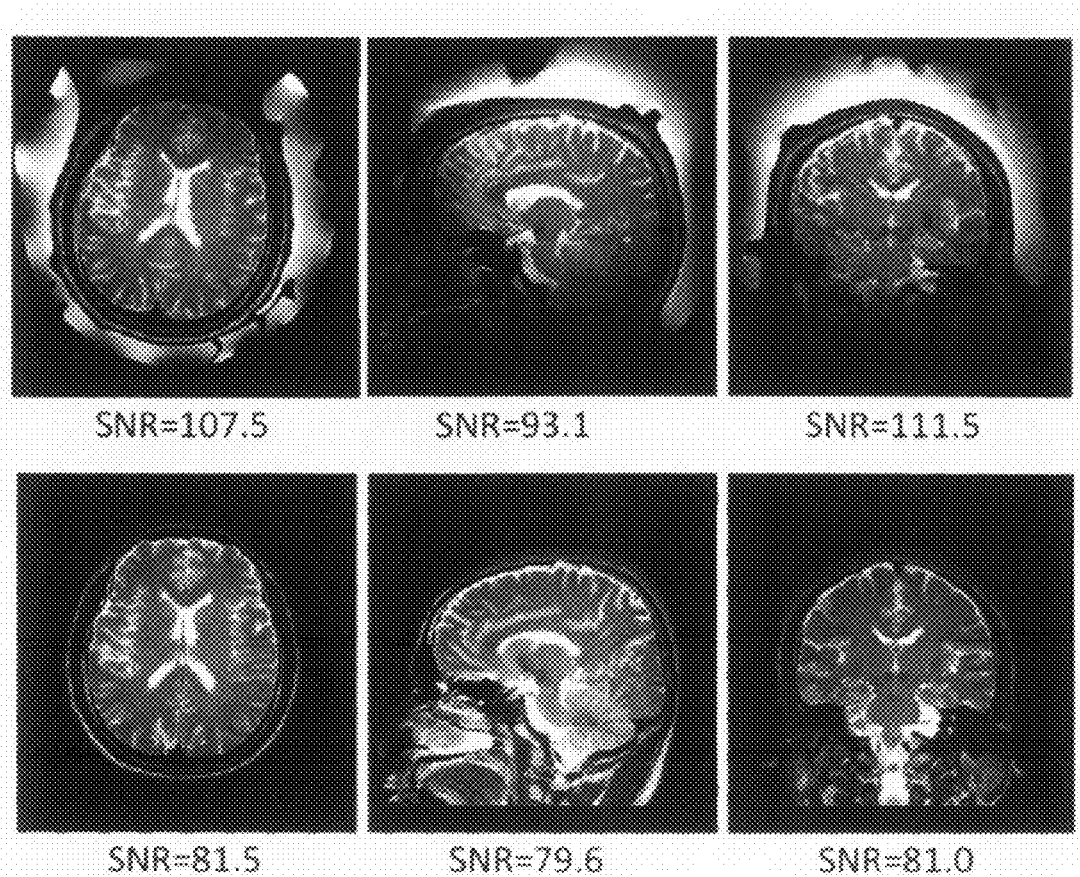
FIG. 4 Axial, sagittal, and coronal images through brain with (top) and without (bottom) HDC-pad. Measured SNR values in regions indicated on FIG. 1 are given under each image.
Figure 6:
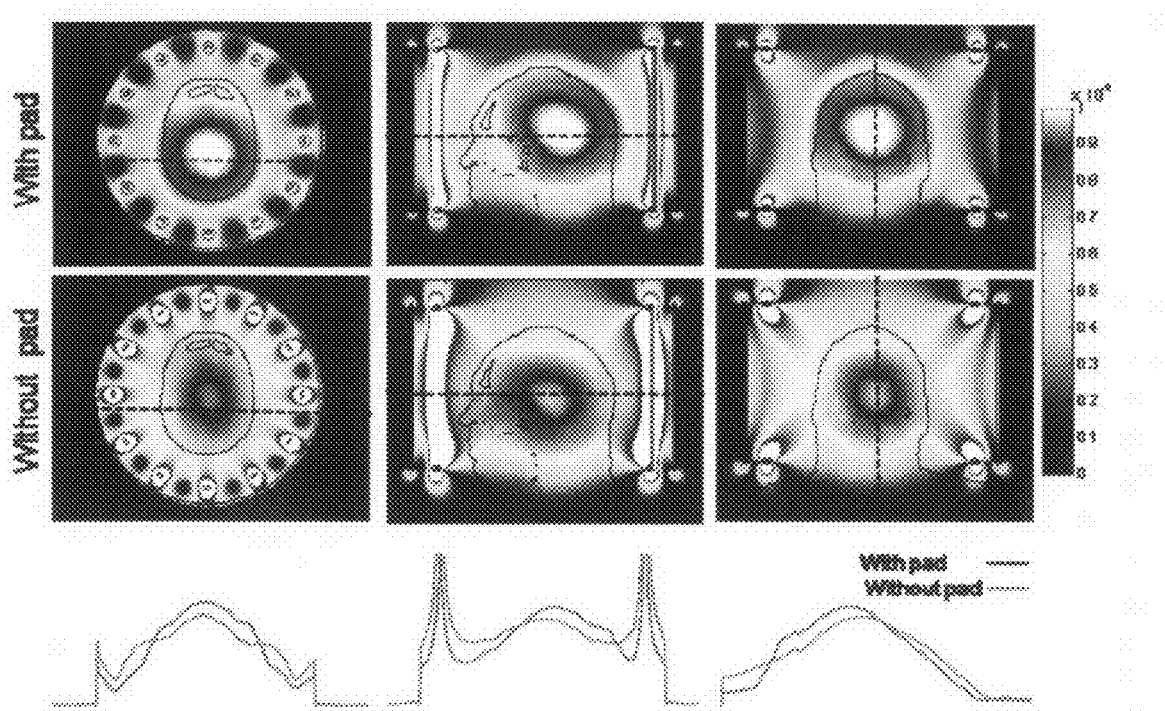

FIG. 4 shows images acquired with and without the HDC-pad on axial, sagittal, and coronal planes. The SNR in the brain measured in the elliptical regions indicated in FIG. 1 is listed below each corresponding image. For all 15 planes acquired, the SNR increased by 20 to 40% (in average, 27%) with addition of the HDC-pad while the overall uniformity of image intensities appear to be similar in both cases. The SNR of repeated experiments are within the same range.

FIG. 5 shows the calculated $B_1^+$ distributions with and without the HDC-pad in three orthogonal planes arranged as in the experimental results. All the fields correspond to 1 W of power delivered to the coil. The calculated $B_1^+$ distributions under the two conditions presented similar characteristics as the in vivo images in FIG. 4. The RF field appears to be greater inside the brain regions surrounded by the HDC-pad but lower in the regions in the face and neck outside of the padded region. $B_1^+$ outside the upper portion of the head and pad is lower when the HDC-pad is present and the same input power is maintained. This can be seen in the line plots at the bottom of the figure, which present $B_1^+$ along the dotted lines in the maps above in FIG. 5. The black and gray lines indicate $B_1^+$ for cases with and without the HDC-pad respectively. The RF field around the coil elements and in between the coil element and shield (seen most clearly in the middle line plot) was reduced more than 70%, indicating less current is required in the coil to maintain the same RF power level when the pad is present. In ROIs similar to those used in the in vivo results, the average $B_1^+$ in the simulation is seen to increase by 12-20% with HDC-pad while the source current in the coil is reduced. These computer modeling results demonstrated that the HDC-pad improves the efficiency of generation of $B_1$ field by a given RF coil, resulting in an increase in image SNR and decrease of RF power required for a given flip angle.

Discussion

Addition of a HDC-pad surrounding the head resulted in a reduction of required RF power by approximately 50% and an increase in image SNR by approximately 27% with a transmit/receive volume coil at 3 T. No obvious local bias field induced by HDC-pad in the entire cerebrum was observed in the images in FIG. 4. In addition, image uniformity within the cerebrum appeared to be somewhat improved. The standard deviation of the signal intensity distribution in the elliptical regions on all 15 images acquired from approximately the same brain volume decreased by an average of 12% with addition of the HDC-pad. The uniformity in this brain area that is normally interference by the so-called bright center spot due to the RF wave effect was reduced markedly.

Comparing images in FIG. 4 acquired with and without the HDC-pad showed that the image intensity in the cerebrum relative to the neck and face is much greater with the HDC-pad than without it. It is likely that this is due to the enhancement of the $B_1$ field for a given input power in the regions that were surrounded by the HDC-pad. $B_1$ field distribution of the coil is altered by the strong displacement currents in the region of the pad, resulting in stronger $B_1$ fields in the vicinity of the HDC-pad. These experimental data suggested that the regional enhancement of the $B_1$ fields in the ROI can be extended to the entire cerebrum with proper coverage by the HDC-pad while the $B_1$ field outside the sample is decreased. As a direct result, average SAR levels for the brain imaging will be lowered with the HDC-pad, and because SNR is proportional to the ratio of the $B_1$ field strength to the square root of the corresponding RF power, SNR is increased with addition of the HDC-pad. The numerical modeling results summarized in FIG. 5 are consistent with the experimental data and clearly demonstrate the enhancement of the $B_1$ field in the brain by the HDC-pad. The $B_1$ field is increased in the entire cerebrum region while outside the brain appears to be reduced by the placement of the HDC-pad when the $B_1^+$ maps are normalized to unit input power. Under this condition, $B_1^+$ is increased in the cerebrum with reduced input current in the coil. This is apparent in the middle line plot, where the two ends of the line pass through coil current elements. Since the magnetic field in the upper portion of the head is relatively high compared to elsewhere, a greater percentage of the input power is also dissipated in that region. To maintain the same total input power as is the case in FIG. 5, the coil requires less current and produces lower $B_1^+$ in regions outside the HDC-pad compared to the case when the HDC-pad is not present. Thus, overall, the presence of the HDC-pad improves efficiency of delivery of both $B_1$ field and RF energy to the section of the head surrounded by the HDC-pad.

Those skilled in the art will appreciate that further development of present invention will lead to an even greater improvement in reducing SAR and improving regional SNR in MRI. The in vivo data presented here at 3 T suggested that HDC-pads around the head or other parts of the anatomy could be used to enhance performance of an RF coil in a variety of cases. A HDC-pad with adjustable volume could be used to enhance RF coil performance while simultaneously providing comfort and reduction of patient motion. This could be particularly beneficial for pediatric patients since most RF coils are designed to accommodate larger adult anatomies. In some cases, there may also be advantages to incorporating dielectric material directly into RF coil constructions. Further developments of presently preferred embodiment include determination of the locations, dimensions, geometries and permittivity distributions of the material for optimal $B_1$ enhancement.

Water was used in this embodiment as a dielectric medium to demonstrate the desired effect of present invention as water has relatively high dielectric constant and low conductivity, is readily available, inexpensive, and nontoxic. From a technical point of view, however, water is unlikely to be the most suitable dielectric material for many intended applications in the art because it produces strong signal that saturates the receiver and decreases the dynamic range of the digitizer and its movements and geometry are difficult to control. Deuterium ($D_2O$) and high dielectric constant material such as barium titanates slurry suspension in the deuterium can be used in replace the water. It is known to the art also that certain ceramic materials has dielectric constant as high as a few thousands, which can be used for the embodiments of the present invention.

Those skilled in the art will appreciate that strategic placement of HDC-pads around the head within a given RF coil at 3 T can result in reduced RF transmission power and improved image SNR throughout the cerebrum, and that with further exploration and development, use of HDC-pads may provide a relatively simple and low-cost method for improving quality and safety of MRI in a variety of applications.

Those skilled in the art will also appreciate that numerous other modifications to the preferred embodiment and other embodiments of present invention are possible within the scope of the invention. These include further developments in optimization of the size, shape, thickness and volume of HDC-pads for specific applications to given body parts or organs for MRI systems with various static magnetic field strengths; in formulation and processing of high dielectric materials used for the HDC-pads; in selection of the values of dielectric constant (permittivity) and in incorporation HDC material in RF coil constructions. Other developments would be implementing HDC-pads and other embodiments of the present invention to the MRI systems with different static magnetic field strengths available.

The scope of the present invention is not intended to be limited to the preferred embodiments described above, but only by any appended claims.

REFERENCES CITED

1. Wang Z, Lin J C, Mao W, Liu W, Smith M B, Collins C M, J Magn Reson Imaging. SAR and temperature: simulations and comparison to regulatory limits for MRI, 2007 August; 26(2):437-41.
2. Alsop D C, Connick T J, Mizsei G. A spiral volume coil for improved RF field homogeneity at high static magnetic field strength. Magn Reson Med 1998; 40:49-54.
3. Abduljalil A M, Kangarlu A, Zhang X, Burgess R E, Robitaille P M. Acquisition of human multislice MR images at 8 Tesla. J Comput Assist Tomogr 1999; 23:335-340.
4. Van de Moortele P F, Akgun C, Adriany G, Moeller S, Ritter J, Collins C M, Smith M B, Vaughan J T, Ugurbil K. B(1) destructive interferences and spatial phase patterns at 7 T with a head transceiver array coil. Magn Reson Med 2005; 54:1503-1518.
5. Vaughan J T, Garwood M, Collins C M, Liu W, DelaBarre L, Adriany G, Andersen P, Merkle H, Goebel R, Smith M B, Ugurbil K. 7 T vs. 4 T: RF power, homogeneity, and signal-to-noise comparison in head images. Magn Reson Med 2001; 46:24-30.
6. Yang Q X, Wang J, Zhang X, Collins C M, Smith M B, Liu H, Zhu X H, Vaughan J T, Ugurbil K, Chen W. Analysis of wave behavior in lossy dielectric samples at high field. Magn Reson Med 2002; 47:982-989.
7. Caserta J, Beck B L, Fitzsimmons J R. Reduction of wave phenomena in high-field MRI experiments using absorbing layers. J Magn Reson 2004; 169:187-195.
8. Wen H, Jaffer F A, Denison T J, Duewell S, Chesnick A S, Balaban R S. The evaluation of dielectric resonators containing H2O or D2O as RF coils for high-field MR imaging and spectroscopy. J Magn Reson B 1996; 110:117-123.
9. Bomsdorf H, Helzel T, Kunz D, Roschmann P, Tschendel O, Wieland J. Spectroscopy and imaging with a 4 tesla whole-body MR system. NMR Biomed 1988; 1:151-158.
10. Foo T K, Hayes C E, Kang Y W. Reduction of RF penetration effects in high field imaging. Magn Reson Med 1992; 23:287-301.
11. Yang Q X, Mao W, Wang J, Smith M B, Lei H, Zhang X, Ugurbil K, Chen W. Manipulation of image intensity distribution at 7.0 T: passive RF shimming and focusing with dielectric materials. J Magn Reson Imaging 2006; 24:197-202.
12. Johnk CTA. Engineering electromagnetic fields and waves. New York: John Wiley & Sons; 1988. p 637.
13. Gabriel C. Compilation of the dielectric properties of body tissues at RF and microwave frequencies. Air Force material command, Brooks Air Force Base, Texas: AUOE-TR-1996-0037; 1996.
14. Park B, Neuberger T, Webb A G, Bigler D C, Collins C M. Faraday Shields within a solenoid coil to reduce sample heating: numerical comparison of designs and experimental verification. J Magn Reson in press.
15. Neufeld A, Landsberg N, Boag A. Dielectric inserts for sensitivity and RF magnetic field enhancement in NMR volume coils. J Magn Reson 2009; 200:49-55.

16. Hoult D I. The sensitivity of the zeugmatographic experiment involving human samples. J Magn Reson 1979; 34:425-433.

The invention claimed is:

1. A spectroscopic method of analyzing a sample, the method comprising:
   identifying a region to be analyzed;
   applying a radiofrequency field from a radiofrequency coil through a high dielectric constant material to the region; and gathering information about the region with a computer, the information gathered from the application of the radiofrequency field to the region;
   wherein the radiofrequency field includes an electric field and a radiofrequency magnetic field, the radiofrequency magnetic field generated by the electric field;
   wherein the radiofrequency coil is positioned with respect to the high dielectric constant material, such that the radiofrequency magnetic field extends through both the region and the high dielectric constant material and increases the signal to noise ratio of all the information gathered.

2. The method of claim 1, further comprising applying the radiofrequency field during magnetic resonance imaging.

3. The method of claim 1, wherein the radiofrequency coil is a phase array coil for a spine, a head, a knee, or an extremity.

4. The method of claim 1, wherein the dielectric includes one or more of a solid, a liquid, a jell, a suspension, and a paste.

5. The method of claim 1, further comprising positioning the high dielectric constant material directly on the radiofrequency coil.

6. The method of claim 1, wherein the radiofrequency field is applied during nuclear magnetic resonance analysis.

7. The method of claim 1, wherein the high dielectric constant material results in a reduction of required radiofrequency power by at least 50%.

8. The method of claim 1, wherein the high dielectric constant material results in an increase in signal to noise ratio by between 20% and 40%.

9. The method of claim 1, wherein the high dielectric constant material is within a pad.

10. The method of claim 9, further comprising conforming the pad to body parts of a mammal.

11. The method of claim 9, further comprising positioning the pad around the neck of a human.

12. The method of claim 9, further comprising positioning the pad around extremities of a mammal.

13. The method of claim 9, wherein the pad is planar.

14. The method of claim 9, further comprising shaping the pad to conform to a human breast.

15. The method of claim 9, further comprising shaping the pad to conform to a pediatric human.

16. The method of claim 9, further comprising shaping the pad to conform to an adult human.

17. A spectroscopic method of analyzing a sample, the method comprising:
    identifying a region to be analyzed;
    applying a radiofrequency field from a radiofrequency coil through a high dielectric constant material to the region; and
    gathering information about the region from the application of the radiofrequency field to the region with a computer;
    wherein the radiofrequency field includes an electric field and a radiofrequency magnetic field, the radiofrequency magnetic field generated by the electric field;
    wherein the radiofrequency coil is positioned with respect to the high dielectric constant material, such that the radiofrequency magnetic field extends through both the region and the high dielectric constant material and reduces the required radiofrequency power.

18. An analytical spectroscopic device, the device adapted for analyzing a region and comprising:
    a high dielectric material configured to surround the region to be analyzed;
    a radiofrequency coil and the high dielectric constant material in an arrangement such that the radiofrequency coil is configured to apply a radiofrequency field to the region only through the high dielectric constant material; and
    a computer configured to gather information about the region resulting from application of the radiofrequency field to the region;
    wherein the radiofrequency field includes an electric field and a radiofrequency magnetic field, the radiofrequency magnetic field generated by the electric field;
    wherein the arrangement of the radiofrequency coil with respect to the high dielectric constant material results in the radiofrequency magnetic field extending through the region and increases the signal to noise ratio of all the information gathered.

* * * * *